(12) United States Patent
Stigall et al.

(10) Patent No.: US 12,178,643 B2
(45) Date of Patent: Dec. 31, 2024

(54) INTRACARDIAC THERAPEUTIC AND DIAGNOSTIC ULTRASOUND DEVICE

(71) Applicant: KONINKLIJKE PHILIPS N.V., Eindhoven (NL)

(72) Inventors: Jeremy Stigall, Carlsbad, CA (US); Princeton Saroha, Ladera Ranch, CA (US); Robert Emmett Kearney, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 326 days.

(21) Appl. No.: 15/998,480

(22) Filed: Aug. 15, 2018

(65) Prior Publication Data

US 2019/0053783 A1    Feb. 21, 2019

Related U.S. Application Data

(60) Provisional application No. 62/545,927, filed on Aug. 15, 2017.

(51) Int. Cl.
*A61B 8/12* (2006.01)
*A61B 8/00* (2006.01)
(Continued)

(52) U.S. Cl.
CPC ............ *A61B 8/12* (2013.01); *A61B 8/445* (2013.01); *A61B 8/4483* (2013.01);
(Continued)

(58) Field of Classification Search
CPC ....... A61B 8/12; A61B 8/445; A61B 17/2202; A61B 2017/22028; A61N 7/022; A61N 2007/0043
See application file for complete search history.

(56) References Cited

U.S. PATENT DOCUMENTS 5,316,000 A * 5/1994 Chapelon ............... A61N 7/022
                                                         601/4
5,630,837 A * 5/1997 Crowley ............... B06B 1/0633
                                                         601/2
(Continued)

FOREIGN PATENT DOCUMENTS

| EP | 2727544 A1 | 5/2014 |
|----|------------|--------|
| WO | 2006060492 A2 | 6/2006 |
| WO | 2008102363 A2 | 8/2008 |

OTHER PUBLICATIONS

Shung "Diagnostic Ultrasound: Imaging and Blood Flow Measurements" 2006 (Year: 2006).*
(Continued)

*Primary Examiner* — Colin T. Sakamoto

(57) ABSTRACT

Systems, methods, and devices for using ultrasound for diagnostic and therapeutic procedures are provided. Ultrasound signals may be transmitted and/or received by ultrasound transducers in an ultrasound device positioned within the anatomy of a patient. The ultrasound transducers may be arranged in an array such that a first segment of the array is configured to transmit ultrasound pulses and receive ultrasound echoes for diagnostic procedures and a second segment of the array is configured to transmit ultrasound pulses for therapeutic procedures. The received ultrasound echoes may be used to generate two- or three-dimensional images of the anatomy.

11 Claims, 7 Drawing Sheets

(51) Int. Cl.
   *A61B 17/22* (2006.01)
   *A61N 7/02* (2006.01)
   *A61B 5/00* (2006.01)
   *A61B 18/00* (2006.01)
   *A61B 18/14* (2006.01)
   *A61N 7/00* (2006.01)

(52) U.S. Cl.
   CPC .............. *A61B 8/4488* (2013.01); *A61B 8/56* (2013.01); *A61B 17/2202* (2013.01); *A61N 7/022* (2013.01); *A61B 5/6852* (2013.01); *A61B 2017/22008* (2013.01); *A61B 2017/22028* (2013.01); *A61B 2018/00404* (2013.01); *A61B 2018/00577* (2013.01); *A61B 18/1492* (2013.01); *A61N 2007/0052* (2013.01); *A61N 2007/0073* (2013.01); *A61N 2007/0078* (2013.01); *A61N 2007/0082* (2013.01); *A61N 2007/0095* (2013.01); *A61N 2007/027* (2013.01)

(56) References Cited

U.S. PATENT DOCUMENTS

| | | |
|---|---|---|
| 6,200,268 B1 | 3/2001 | Vince et al. |
| 6,381,350 B1 | 4/2002 | Klingensmith et al. |
| 7,074,188 B2 | 7/2006 | Nair et al. |
| 7,175,597 B2 | 2/2007 | Vince et al. |
| 7,215,802 B2 | 5/2007 | Klingensmith et al. |
| 7,359,554 B2 | 4/2008 | Klingensmith et al. |
| 7,463,759 B2 | 12/2008 | Klingensmith et al. |
| 2004/0073114 A1* | 4/2004 | Oliver .............. A61B 17/2202 600/439 |
| 2005/0096542 A1 | 5/2005 | Weng et al. |
| 2005/0267453 A1* | 12/2005 | Wong ................ A61B 8/4488 606/27 |
| 2006/0206028 A1* | 9/2006 | Lee .................... A61B 17/3203 600/471 |
| 2007/0073135 A1* | 3/2007 | Lee ..................... A61B 8/4488 600/407 |
| 2012/0143063 A1* | 6/2012 | Robinson ............... A61B 8/145 600/472 |
| 2013/0261455 A1 | 10/2013 | Thapliyal et al. |
| 2014/0005521 A1* | 1/2014 | Kohler ................ A61B 6/4057 600/411 |
| 2014/0270430 A1 | 9/2014 | Nair |
| 2014/0276050 A1* | 9/2014 | Jenson ................... A61B 8/085 600/439 |
| 2015/0305708 A1* | 10/2015 | Stigall ............... A61B 5/02007 600/467 |
| 2016/0008636 A1* | 1/2016 | Warnking ............. A61B 8/483 600/411 |
| 2018/0064415 A1* | 3/2018 | Zhai .................... A61B 8/0883 |
| 2021/0007759 A1* | 1/2021 | Jiang .................... A61B 18/26 |

OTHER PUBLICATIONS

American Institute of Physics "Highlights of upcoming acoustics meeting in New Orleans" EurekAlert.org Nov. 2007 (Year: 2007).*

Lewis et al., "A Phantom feasibility study of acoustic enhanced drug diffusion in neurological tissue" Nov. 1, 2007 (Year: 2007).*

Dance et al., "Diagnostic Radiology Physics", International Atomic Energy Agency, Vienna, Austria, 2014 (Year: 2014).*

Walker et al., "A Digitally Controlled CCD Dynamically Focussed Phased Array," 1975 Ultrasonics Symposium, Los Angeles, CA, USA, 1975, pp. 80-83 (Year: 1975).*

Constanciel, et al: "Design and evaluation of a transesophageal HIFU probe for ultrasound-guided cardiac ablation: simulation of a HIFU mini-maze procedure and preliminary ex vivo trials", IEEE Transactions on Ultrasonics, Ferroelectrics, and Frequency Control, vol. 60, No. 9, Sep. 2013.

* cited by examiner

INTRACARDIAC THERAPEUTIC AND DIAGNOSTIC ULTRASOUND DEVICE

TECHNICAL FIELD

The present disclosure relates generally to ultrasound devices, and in particular, ultrasound devices with transducers that may be used for therapeutic and diagnostic applications.

BACKGROUND

Diagnostic and therapeutic ultrasound catheters have been designed for use inside many areas of the human body. In the cardiovascular system, a common diagnostic ultrasound methods is intraluminal ultrasound imaging with intra-cardiac echocardiography (ICE) being a specific example of intraluminal imaging. Typically, a single rotating transducer or an array of transducer elements is used to transmit ultrasound at the tips of the catheters. The same transducers (or separate transducers) are used to receive echoes from the tissue. A signal generated from the echoes is transferred to a console which allows for the processing, storing, display, or manipulation of the ultrasound-related data.

Intraluminal imaging catheters such as ICE catheters (e.g., Siemens Acunav, St. Jude ViewFlex) are usually used to image heart and surrounding structures, for example, to guide and facilitate medical procedures, such as transseptal lumen punctures, left atrial appendage closures, atrial fibrillation ablation, and valve repairs. Commercially-available ICE catheters have distal ends which can be articulated by a steering mechanism located in a handle at the proximal end of the catheter. For example, an intraluminal imaging catheter such as an ICE catheter may be inserted through the femoral or jugular vein when accessing the anatomy, and steered in the heart to acquire images necessary to the safety of the medical procedures.

Existing ICE catheters are used only for imaging procedures. After imaging procedures are complete, the catheters are usually removed and other systems are inserted into the vasculature of a patient to treat areas of interest identified by the imaging procedures. The removal and insertion of multiple tools may be time consuming and may increase health risks to the patient.

SUMMARY

An ultrasound system is provided by the present disclosure. The ultrasound system can include an ultrasound device that is configured to be placed inside of the anatomy of a patient. The ultrasound device may include a transducer array with a number of transducer elements. The transducer array may include a first portion and a second portion. The first portion may be used for diagnostic procedures that may include transmitting ultrasound signals and receiving ultrasound echoes with the first portion. The second portion may be used for therapeutic procedures including transmitting ultrasound signals. The ultrasound signals transmitted for therapeutic purposes may have a lower frequency than those transmitted for diagnostic purposes. Exemplary technical advancements described herein include an ultrasound system that may be used to image and treat a patient without removing and replacing equipment. Furthermore, the ultrasound system may be configured to provide ultrasound signals at different angles without physically moving the ultrasound device.

An ultrasound system is provided by the present disclosure, which may include: an ultrasound device that may include: a flexible elongate member configured to be positioned within anatomy of a patient, the flexible elongate member comprising a proximal portion and a distal portion; and an ultrasound transducer array positioned at the distal portion of the flexible elongate member, wherein the ultrasound transducer array includes a plurality of transducer elements arranged in a first segment and a second segment, wherein the first segment is configured to emit a first ultrasound signal with a first frequency and the second segment is configured to emit a second ultrasound signal with a second frequency different than the first frequency.

In some embodiments, the second frequency is lower than the first frequency. In particular, the first frequency may be between 10 MHz and 70 MHz and the second frequency is between 1 kHz and 5 MHz. The ultrasound transducer array may be a two-dimensional array, wherein the first segment is disposed on a first portion of the two-dimensional array and the second segment is disposed on a second portion of the two-dimensional array adjacent the first portion. In some embodiments, the first segment comprises a high resonant frequency material and the second segment comprises a low resonant frequency material. The ultrasound transducer array may include at least one of PZT, CMUT, or PMUT.

In some embodiments, the first segment of the ultrasound transducer array is configured to receive ultrasound echoes reflected from the anatomy and associated with the first ultrasound signal. The ultrasound system may further include a computing device in communication with the ultrasound transducer array and configured to produce an ultrasound image based on the received ultrasound echoes. The system may further include a controller disposed at the distal portion of the flexible elongate member and in communication with the ultrasound transducer array. In some embodiments, the ultrasound transducer array is configured to direct the second ultrasound signal to a first portion of anatomy and a second portion of anatomy different from the first portion of anatomy without moving the ultrasound transducer array.

The ultrasound device may further include a switch to selectively switch between transmitting signals with the first segment and the second segment. The ultrasound device may further include a substrate including electrical conductors connected to the ultrasound transducer array, the electrical conductors configured to selectively switch between transmitting signals with the first segment and the second segment. The flexible elongate member may include a first cable configured to control transmission of signals of the first segment and a second cable configured to control transmission of signals of the second segment. The flexible elongate member may include a third cable configured to control transmission of signals of both the first segment and the second segment.

A method of transmitting ultrasound signals is provided by the present disclosure, which may include: transmitting, with a first segment of an ultrasound transducer array of an ultrasound device positioned within anatomy of a patient, a first ultrasound signal with a first frequency to image an area of interest of the anatomy; receiving, with the first segment of the ultrasound transducer array, ultrasound echoes reflected from the anatomy and associated with the first ultrasound signal; and transmitting, with a second segment of the ultrasound transducer array, a second ultrasound signal with a second frequency to an area of interest within the anatomy.

In some embodiments, the method further includes generating, with a controller, an image of the area of interest based on the second ultrasound signal. The method may include generating a treatment plan based on the image of the area of interest. The method may include transmitting, with the second segment of the ultrasound transducer array, the second ultrasound signal to perform a therapeutic procedure based on the treatment plan. The therapeutic procedure may include an ultrasound cavitation procedure that includes forming ultrasound cuts into calcification within the anatomy. The therapeutic procedure may include preparing a portion of the anatomy for delivery of medication.

In some embodiments, the second ultrasound signal has a lower frequency than the first ultrasound signal. In particular, the frequency of the first ultrasound signal may be between 10 MHz and 70 MHz and a frequency of the second ultrasound signal may be between 1 kHz and 5 MHz. The method may include placing the ultrasound device within the anatomy of the patient. The method may include directing transmission of the second ultrasound signal from the second segment to a first portion of the area of interest and directing transmission of a third ultrasound signal from the second segment to a second portion of the area of interest different than the first portion of the area of interest without moving the ultrasound transducer array.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
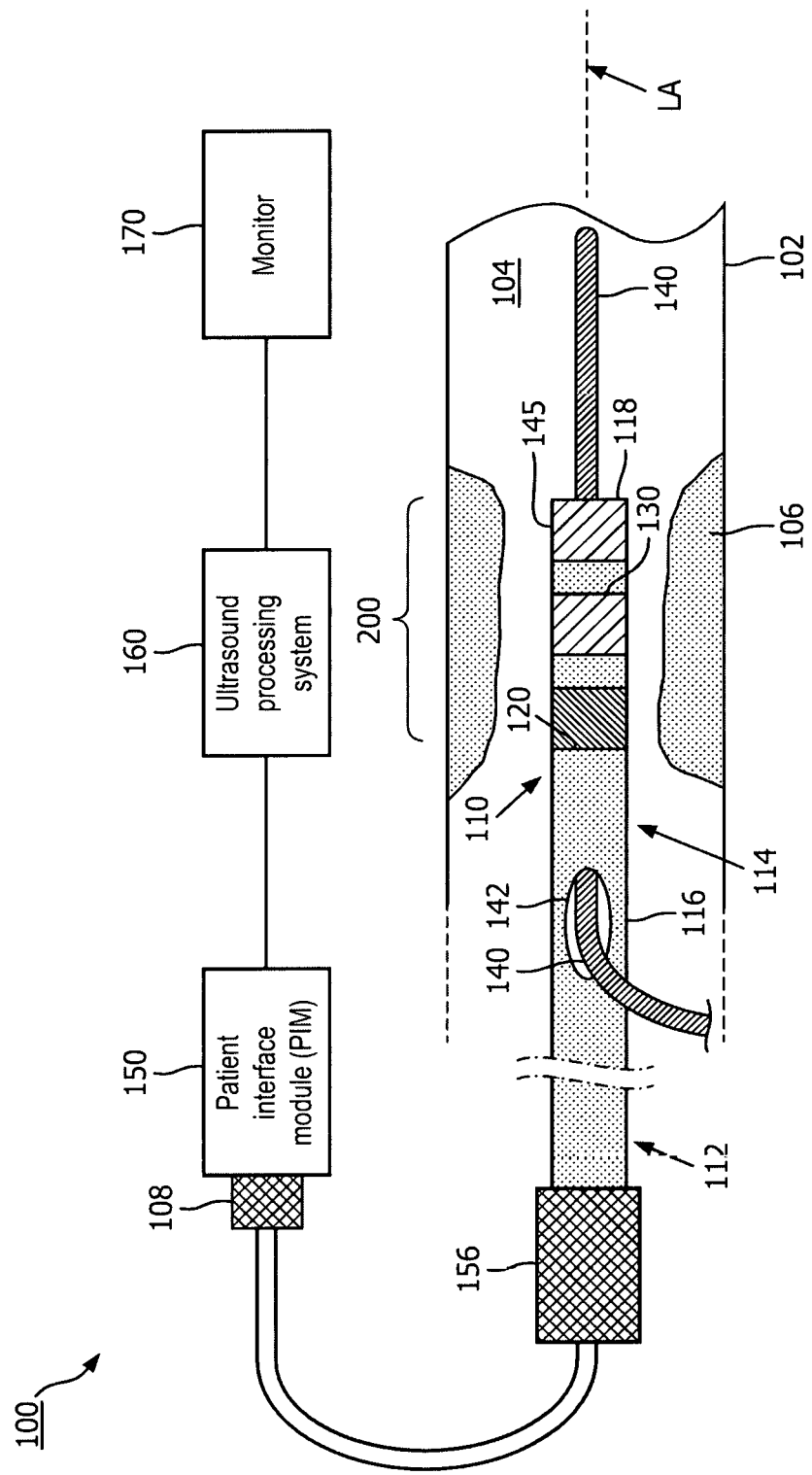
FIG. 1 is a schematic diagram of an ultrasound system according to embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the ultrasound system is described in terms of transmitting ultrasound signals and receiving ultrasound echoes, it is understood that it is not intended to be limited to this application. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an ultrasound system 100 according to some embodiments of the present disclosure. The system 100 can include an ultrasound device 110, a patient interface module (PIM) 150, an ultrasound processing system 160, and/or a monitor 170. The ultrasound device 110 is structurally arranged (e.g., sized and/or shaped) to be positioned within anatomy 102 of a patient. The ultrasound device 110 obtains ultrasound imaging data from within the anatomy 102 and applies ultrasound therapy to the anatomy 102. The ultrasound processing system 160 can control the acquisition of ultrasound imaging data and/or the application of ultrasound therapy, and generates an image of the anatomy 102 (using the ultrasound imaging data received via the PIM 150) that is displayed on the monitor 170.

Generally, the ultrasound device 110 can be a catheter, a guide catheter, or a guide wire. The ultrasound device 110 includes a flexible elongate member 116. As used herein, "elongate member" or "flexible elongate member" includes at least any thin, long, flexible structure structurally arranged (e.g., sized and/or shaped) to be positioned within a lumen 104 of the anatomy 102. For example, a distal portion 114 of the flexible elongate member 116 is positioned within the lumen 104, while a proximal portion 112 of the flexible elongate member 116 is positioned outside of the body of the patient. The flexible elongate member 116 can include a longitudinal axis LA. In some instances, the longitudinal axis LA can be a central longitudinal axis of the flexible elongate member 116. In some embodiments, the flexible elongate member 116 can include one or more polymer/plastic layers formed of various grades of nylon, Pebax, polymer composites, polyimides, and/or Teflon. In some embodiments, the flexible elongate member 116 can include one or more layers of braided metallic and/or polymer strands. The braided layer(s) can be tightly or loosely braided in any suitable configuration, including any suitable per in count (pic). In some embodiments, the flexible elongate member 116 can include one or more metallic and/or polymer coils. All or a portion of the flexible elongate member 116 may have any suitable geometric cross-sectional profile (e.g., circular, oval, rectangular, square, elliptical, etc.) or non-geometric cross-sectional profile. For example, the flexible elongate member 116 can have a generally cylindrical profile with a circular cross-sectional profile that defines an outer diameter of the flexible elongate member 116. For example, the outer diameter of the flexible elongate member 116 can be any suitable value for positioning within the anatomy 102, including between approximately 1 Fr and approximately 15 Fr, including values such as 3.5 Fr, 5 Fr, 7 Fr, 8.2 Fr, 9 Fr, and/or other suitable values both larger and smaller.

The ultrasound device 110 may or may not include one or more lumens extending along all or a portion of the length of the flexible elongate member 116. The lumen of the ultrasound device 110 can be structurally arranged (e.g., sized and/or shaped) to receive and/or guide one or more other diagnostic and/or therapeutic instruments. If the ultrasound device 110 includes lumen(s), the lumen(s) may be centered or offset with respect to the cross-sectional profile of the device 110. In the illustrated embodiment, the ultrasound device 110 is a catheter and includes a lumen at the distal portion 114 of the flexible elongate member 116. A guide wire 140 extends through the lumen of the ultrasound device 110 between an exit/entry port 142 and an exit/entry port at a distal end 118 of the flexible elongate member 116. Generally, the guide wire 140 is a thin, long, flexible structure that is structurally arranged (e.g., sized and/or shaped) to be disposed within the lumen 104 of the anatomy 102. During a diagnostic and/or therapeutic procedure, a medical professional typically first inserts the guide wire 140 into the lumen 104 of the anatomy 102 and moves the guide wire 140 to a desired location within the anatomy 102, such as adjacent to an occlusion 106. The guide wire 140 facilitates introduction and positioning of one or more other diagnostic and/or therapeutic instruments, including the ultrasound device 110, at the desired location within the anatomy 102. For example, the ultrasound device 110 moves through the lumen 104 of the anatomy 102 along the guide wire 140. In some embodiments, the lumen of the ultrasound device 110 can extend along the entire length of the flexible elongate member 116. In the illustrated embodiment, the exit/entry port 142 is positioned proximally of components 120, 130, and 145 of the ultrasound device 110. In some embodiments, the exit/entry port 142, the exit/entry port at the distal end 118, and/or the lumen of the ultrasound device 110 is positioned distally of the components 120, 130, and 145. In some embodiments, the ultrasound device 110 is not used with a guide wire, and the exit/entry port 142 can be omitted from the ultrasound device 110.

The anatomy 102 may represent any fluid-filled or surrounded structures, both natural and man-made. For example, the anatomy 102 can be within the body of a patient. Fluid can flow through the lumen 104 of the anatomy 102. In some instances, the ultrasound device 110 can be referenced as an intraluminal device. The anatomy 102 can be a vessel, such as a blood vessel, in which blood flows through the lumen 104. In some instances, the ultrasound device 110 can be referenced as an intravascular device. In various embodiments, the blood vessel is an artery or a vein of a patient's vascular system, including cardiac vasculature, peripheral vasculature, neural vasculature, renal vasculature, and/or any other suitable anatomy/lumen inside the body. The anatomy 102 can be tortuous in some instances. For example, the device 110 may be used to examine any number of anatomical locations and tissue types, including without limitation, organs including the liver, heart, kidneys, gall bladder, pancreas, lungs, esophagus; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 110 may be used to examine man-made structures such as, but without limitation, heart valves, stents, shunts, filters and other devices.

The occlusion 106 of the anatomy 102 is generally representative of any blockage or other structural arrangement that results in a restriction to the flow of fluid through the lumen 104, for example, in a manner that is deleterious to the health of the patient. For example, the occlusion 106 narrows the lumen 104 such that the cross-sectional area of the lumen 104 and/or the available space for fluid to flow through the lumen 104 is decreased. Where the anatomy 102 is a blood vessel, the occlusion 106 may be a result of plaque buildup, including without limitation plaque components such as fibrous, fibro-lipidic (fibro fatty), necrotic core, calcified (dense calcium), blood, fresh thrombus, and/or mature thrombus. In some instances, the occlusion 106 can be referenced as thrombus, a stenosis, and/or a lesion. Generally, the composition of the occlusion 106 will depend on the type of anatomy being evaluated. Healthier portions of the anatomy 102 may have a uniform or symmetrical profile (e.g., a cylindrical profile with a circular cross-sectional profile). The occlusion 106 may not have a uniform or symmetrical profile. Accordingly, diseased portions of the anatomy 102, with the occlusion 106, will have a non-symmetric and/or otherwise irregular profile. While the anatomy 102 is illustrated in FIG. 1 as having a single occlusion 106, it is understood that the devices, systems, and methods described herein have similar application for anatomy having multiple occlusions.

The ultrasound device 110 includes ultrasound structures 120 and 130 at the distal portion 114 of the flexible elongate member 116. The structures 120 and 130 are configured to emit ultrasonic energy into the anatomy 102 while the device 110 is positioned within the lumen 104. In some embodiments, the two ultrasound structures 120 and 130 are distinct. In other embodiments, the two structures 120 and 130 are the same ultrasound component or part of the same ultrasound component. One of the structures 120, 130 is configured for diagnostic use, while the other of the structures 120, 130 is configured for therapeutic use. For example, the structures 120, 130 can emit different frequencies of ultrasonic energy into the anatomy 102 depending on whether the ultrasonic energy is being used for diagnosis, such as imaging, and/or treatment.

In some embodiments, the structures 120 and/or 130 include ultrasound transducer(s). For example, the ultrasound structures 120 and/or 130 can be configured to generate and emit ultrasound energy into the anatomy 102 in response to being activated by an electrical signal. In some embodiments, the structures 120 and/or 130 include a single ultrasound transducer. In some embodiments, the structures 120 and/or 130 include an ultrasound transducer array including more than one ultrasound transducer. For example, an ultrasound transducer array can include any suitable number of individual transducers between 2 transducers and 1000 transducers, including values such as 2 transducers, 4 transducers, 36 transducers, 64 transducers, 128 transducers, 500 transducers, 812 transducers, and/or other values both larger and smaller. The ultrasound transducer array 120 and/or 130 can be any suitable configuration, such as phased array including a planar array, a curved array, a circumferential array, an annular array, etc. For example, the ultrasound transducer array 120 and/or 130 can be a one-dimensional array or a two-dimensional array in some instances. In some instances, the structures 120 and/or 130 can be a rotational ultrasound device. The active area of the ultrasound structures 120 and/or 130 can include one or more transducer materials and/or one or more segments of ultrasound elements (e.g., one or more rows, one or more columns, and/or one or more orientations) that can be uniformly or independently controlled and activated. The active area of the ultrasound structures 120 and/or 130 can be patterned or structured in various basic or complex geometries. The structures 120 and/or 130 can be disposed in a side-looking orientation (e.g., ultrasonic energy emitted perpendicular and/or orthogonal to the longitudinal axis LA) and/or a forward-looking looking orientation (e.g., ultrasonic energy emitted parallel to and/or along the longitudinal axis LA). In some instances, the structures 120 and/or 130 is structurally arranged to emit and/or receive ultrasonic energy at an oblique angle relative to the longitudinal axis LA, in a proximal or distal direction. In some embodiments, ultrasonic energy emission can be electronically steered by selective triggering of one or more transducer elements of the array in structures 120 and/or 130.

The ultrasound transducer(s) of the structures 120 and/or 130 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. Depending on the transducer material, the manufacturing process for ultrasound transducer(s) can include dicing, kerfing, grinding, sputtering, wafer technologies (e.g., SMA, sacrificial layer deposition), other suitable processes, and/or combinations thereof.

In some embodiments, the structure 120 is configured to obtain ultrasound imaging data associated with the anatomy 102, such as the occlusion 106. The ultrasound imaging data obtained by the structure 120 can be used by a medical professional to diagnose the patient, including evaluating the occlusion 106 of the anatomy 102. For imaging, the structure 120 can be configured to both emit ultrasonic energy into the lumen 104 and/or the anatomy 102, and to receive reflected ultrasound echoes representative of fluid and/or tissue of lumen 104 and/or the anatomy 102. As described herein, the structure 120 can be an ultrasound imaging element, such as an ultrasound transducer and/or an ultrasound transducer array. For example, the ultrasound imaging element 120 generates and emits ultrasound energy into the anatomy 102 in response to transmission of an electrical signal to the structure 120. For imaging, the ultrasound imaging element 120 generates and transmits an electrical signal representative of the received reflected ultrasound echoes from the anatomy 102 (e.g., to the PIM 150 and/or ultrasound processing system 160). In various embodiments, the structure 120 can obtain imaging data associated with intravascular ultrasound (IVUS) imaging, forward looking intravascular ultrasound (FL-IVUS) imaging, intravascular photoacoustic (IVPA) imaging, intracardiac echocardiography (ICE), transesophageal echocardiography (TEE), and/or other suitable imaging modalities.

For diagnosis and/or imaging, the center frequency of the ultrasound structure 120 can be between 10 MHz and 70 MHz, for example, including values such as 10 MHz, 20 MHz, 40 MHz, 45 MHz, 60 MHz, and/or other suitable values both larger and smaller. For example, lower frequencies (e.g., 10 MHz, 20 MHz) can advantageously penetrate further into the anatomy 102, such that more of the anatomy 102 is visible in the ultrasound images. Higher frequencies (e.g., 45 MHz, 60 MHz) can be better suited to generate more detailed ultrasound images of the anatomy 102 and/or fluid within the lumen 104. In some embodiments, the frequency of the ultrasound structure 120 is tunable. For imaging, in some instances, the ultrasound structure 120 can be tuned to receive wavelengths associated with the center frequency and/or one or more harmonics of the center frequency. In some instances, the frequency of the emitted ultrasonic energy can be modified by the voltage of the applied electrical signal and/or the application of a biasing voltage to the ultrasound structure 120.

In some embodiments, the structure 130 is configured to apply an ultrasound therapy to the anatomy 102, such as the occlusion 106. For example, the structure 130 emits sound waves that damage the structure of the occlusion 106. In that regard, the device 110 and/or the structure 130 can be referenced as a lithotripsy device. The ultrasonic energy emitted by the structure 130 can create micro fractures in the occlusion 106. For example, the structure 130 can deliver ultrasonic energy in a targeted manner to cause cavitation (e.g., wave force cavitation, thermal cavitation, etc.) of the occlusion 106. Delivery of ultrasound therapy by the structure 130 advantageously facilitates thrombus dilution and/or vessel preparation. For example, ultrasound therapy can be applied prior to delivery of a pharmacological agent to the anatomy 102. The pharmacological agent can be a thrombolytic agent, a fibrinolytic agent, plasmin, plasmid, tissue plasminogen activator, urokinase, streptokinase, collagenace, hepranoid, anti-thrombin drug, any other suitable drug, and/or combinations thereof. As described herein, Pharmacological uptake can be advantageously improved as a result of the degradation of the occlusion 106 by the ultrasonic energy. By compromising the structure of the occlusion 106, additional surface area is available for the pharmacological agent to contact and/or penetrate the anatomy 102. Accordingly, the efficacy of the treatment and the health of the patient are improved.

In some embodiments, the structure 130 is an ultrasound element, such as an ultrasound transducer and/or ultrasound transducer array. For example, the ultrasound processing system 160 can be configured to generate and emit ultrasound energy into the anatomy 102 in response to transmission of an electrical signal to the structure 130. Unlike the structure 120, which is used of ultrasound imaging, the structure 130 need not be configured to receive ultrasonic echoes reflected the anatomy 102 and generate a representative electrical signal. For example, in some embodiments, the structure 130 is not an ultrasound element that generates ultrasound energy. Rather, the structure 130 can be an intermediate component that is configured to deliver ultrasound energy generated an ultrasound component separate from the device 110 (e.g., an external ultrasound transducer positioned outside of the body of the patient). For ultrasound therapy, the center frequency of the ultrasound structure 130 can be between 1 kHz and 5 MHz, for example, including values such as 50 kHz, 500 kHz, 1 MHz, 3 MHz, and/or other suitable values both larger and smaller. In some embodiments, the frequency of the ultrasound structure 130 is tunable. For example, the frequency of the emitted ultrasonic energy can be modified by the voltage of the applied electrical signal and/or the application of a biasing voltage to the ultrasound structure 130.

In some embodiments, such as when the structures 120 and 130 both include ultrasound transducers, the structures 120 and 130 can be configured to generate and to emit ultrasound energy, and to generate electrical signals representative of the received ultrasound echoes. One of the structures 120, 130 can be operated in diagnostic and/or imaging mode (generates and emits ultrasound energy, and generates electrical signals representative of the received ultrasound echoes), while the other of the structures 120, 130 is operated in therapeutic mode (generates and/or emits ultrasound energy).

In some embodiments, the ultrasound device 110 includes a treatment component 145. For example, the treatment component 145 can include a balloon, a stent, a needle, an ablation electrode, mechanical cutting component, a rotational cutting device, an aspiration device, and/or other suitable devices. The treatment component 145 can be a targeted drug delivery device, a drug coated balloon, a drug coated stent, and/or other suitable device configured to deliver a pharmacological agent to the anatomy 102, such as the occlusion 106. For example, the pharmacological agent can be delivered to the anatomy 102 by the treatment component 145 after the ultrasound therapy is applied to the anatomy 102 by the ultrasound structure 130. In other embodiments, the ultrasound device 110 omits the treatment component 145.

Generally, the components 120, 130, and/or 145 are positioned at the distal portion of the flexible elongate member 116. The relative positioning of the components 120, 130, and/or 140 can vary in different embodiments. In the illustrated embodiment, the diagnostic and/or imaging ultrasound structure 120 is positioned proximally of the therapeutic ultrasound structure 130. In other embodiments, the therapeutic ultrasound structure 130 is positioned proximally of the diagnostic and/or imaging ultrasound structure 120. In embodiments which include the treatment component 145, the treatment component 145 can be positioned proximally of the ultrasound structures 120 and/or 130, distally of the ultrasound structures 120 and/or 130, or between the ultrasound structures 120 and/or 130.

The ultrasound structures 120 and/or 130 can include one or more electrical conductors extending along the length from the flexible elongate member 116. The electrical conductor(s) are in communication with the ultrasound structures 120, 130 at the distal portion 114, and an interface 156 at the proximal portion 112. The electrical conductors carry electrical signals between the ultrasound processing system 160 and the ultrasound structures 120, 130. For example, activation and/or control signals can be transmitted from the ultrasound processing system 160 to the ultrasound structures 120, 130 via the electrical conductors. Electrical signals representative of the reflected ultrasound echoes can be transmitted from the ultrasound structures 120 and/or 130 to the ultrasound processing system 160 via the electrical conductors. In some embodiments, the same electrical conductors can be used for communication between the ultrasound processing system 160 and the ultrasound structures 120 and/or 130. In other embodiments, different electrical conductors of the device 110 can be used for communication between the ultrasound processing system 160 and the ultrasound structure 120, and between the ultrasound processing system 160 and the ultrasound structure 130.

The ultrasound device 110 includes an interface 156 at the proximal portion 112 of the flexible elongate member 116. In some embodiments, the interface 156 can include a handle. For example, handle can include one or more actuation mechanisms to control movement of the device 110, such as deflection of the distal portion 114. In some embodiments, the interface 156 can include a telescoping mechanism that allows for pullback of the device 110 through the lumen. In some embodiments, the interface 156 can include a rotation mechanism to rotate one or more components of the device 110 (e.g., the flexible elongate member 116, the ultrasound structures 120, 130). In some embodiments, the interface 156 includes a user interface component (e.g., one or more buttons, a switch, etc.) for a medical professional to selectively activate the ultrasound structure 120 for imaging or the ultrasound structure 130 for therapy. In other embodiments, a user interface component of the PIM 150, the ultrasound processing system 160 and/or the monitor 170 allows a medical profession to selectively activate the ultrasound structure 120 for imaging or the ultrasound structure 130 for therapy. A conduit including, e.g., electrical conductors, extends between the interface 156 and the connector 108. The connector 108 can be configured to mechanically and/or electrically couple the device 110 to the PIM 150.

The ultrasound processing system 160, the PIM 150, and/or the ultrasound device 110 (e.g., the interface 156, the ultrasound structures 120 and/or 130, etc.) can include one or more controllers. The controllers can be integrated circuits, such as application specific integrated circuits (ASIC), in some embodiments. The controllers can be configured to select the particular transducer element(s) to be used for transmit and/or receive, to provide the transmit trigger signals to activate the transmitter circuitry to generate an electrical pulse to excite the selected transducer element(s), and/or to accept amplified echo signals received from the selected transducer element(s) via amplifiers of controllers. Multiple ASIC configurations with various numbers of master circuits and slave circuits can be used to create a single ultrasound wave or multi-firing ultrasound wave device.

In some embodiments, the PIM 150 performs preliminary processing of the ultrasound echo data prior to relaying the data to the computer or console. In examples of such embodiments, the PIM 150 performs amplification, filtering, and/or aggregating of the data. In an embodiment, the PIM 150 also supplies high- and low-voltage DC power to support operation of the device 110 including circuitry associated with the ultrasound structures 120 and/or 130. The PIM 150 can be an isolation device as, in various surgical settings, patient safety requirements mandate physical and electrical isolation of the patient from one or more high voltage components.

The ultrasound processing system 160 receives imaging data (e.g., electrical signals representative of the ultrasound echo data) from the ultrasound structure 120 by way of the PIM 150. The ultrasound processing system 160 can include processing circuit, such as processor and/or memory. The ultrasound processing system 160 processes the data to reconstruct an image of the anatomy. The ultrasound processing system 160 outputs image data such that an image of the anatomy 102, such as a cross-sectional IVUS image of a vessel, is displayed on the monitor 170. The ultrasound processing system 160 and/or the monitor 170 can include one or more user interface elements (e.g., touchscreen, keyboard, mouse, virtual buttons on a graphical user interface, physical buttons, etc.) to allow a medical professional to control the device 110, including one or more parameters of the ultrasound structures 120, 130.

Figure 2:
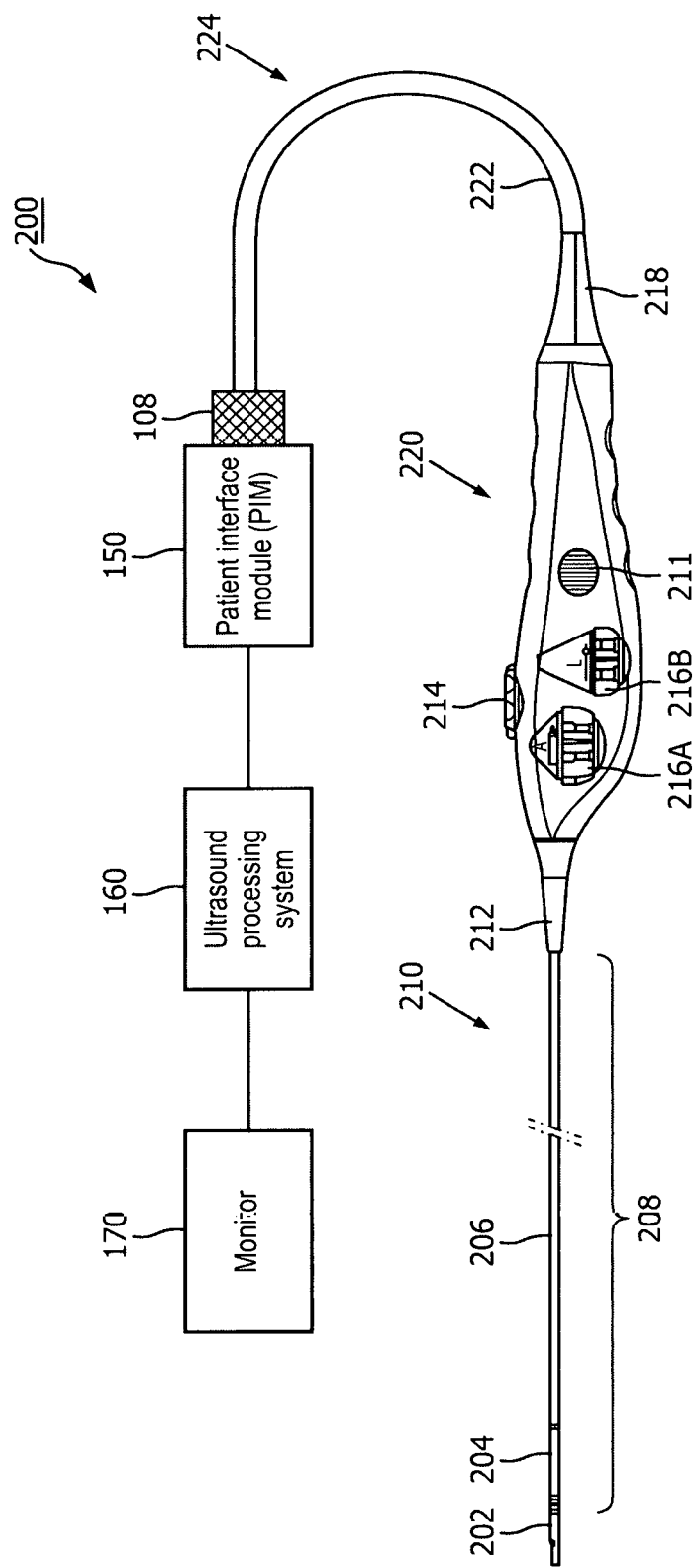
FIG. 2 is a schematic diagram of an ultrasound system including a handle according to embodiments of the present disclosure.

FIG. 2 is a schematic diagram of an ultrasound system 200 according to embodiments of the present disclosure. The ultrasound system 200 may illustrate similar aspects to the ultrasound system 100 as shown in FIG. 1. In particular, the ultrasound system 200 may have the same functionality as the ultrasound system 100 as well as additional features that are described in more detail with reference to FIGS. 2-7. The ultrasound system 200 may include an ultrasound device 210, a connector 224, a PIM 150, an ultrasound processing system 160, and a monitor 170. The ultrasound device 210 may include a tip member 202 at the tip of a flexible elongate member 208 and a handle 220. In some embodiments, the tip member 202 may be used for diagnostic purposes (i.e., imaging of anatomy) as well as therapeutic purposes (i.e., treating portions of anatomy). The flexible elongate member 208 may include a distal portion 204 and a proximal portion 206. The distal end of the distal portion 204 may be attached to the tip member 202. The proximal end of the proximal portion 206 may be attached to the handle 220, for example, by a resilient strain reliever 212. The handle 220 may be used for manipulation and/or manual control of the ultrasound device 210. The tip member 202 may include an imaging core with ultrasound transducer elements and associated circuitry. The handle 220 may include actuators 216, a clutch 214, and other steering control components for steering the ultrasound device 210. The steering may include deflecting the tip member 202 and the distal portion 204, as described in greater details herein.

The handle 220 may be connected to the connector 224 via a second strain reliever 218 and a connection cable 222. The connector 224 may be configured to provide suitable configurations for interconnecting the PIM 150, ultrasound processing system 160, and monitor 170 to the tip member 202. In operation, a physician or a clinician may advance the flexible elongate member 208 into the anatomy of the patient, such as within a vessel or other structure within the heart of the patient. By controlling the actuators 216 and the clutch 214 on the handle 220, the physician or clinician can steer the flexible elongate member 208 to a position near an area of interest to be imaged. For example, a first actuator 216A may deflect the tip member 202 and the distal portion 204 in a left-right plane and a second actuator 216B may deflect the tip member 202 and the distal portion 204 in an anterior-posterior plane. The clutch 214 may include a locking mechanism to lock the positions of the actuators 216, and in effect, lock the deflection of the flexible elongate member 208 while the tip member 202 is used to image or treat the area of interest.

In some embodiments, the tip member 202 may be used for diagnostic processes and therapeutic processes. A diagnostic process may include imaging areas of interest by activating the ultrasound transducer elements on the tip member 202 to produce ultrasonic energy. This ultrasound energy may be referred to as ultrasound signals which may be directed into a portion of the anatomy from the transducer assembly. A portion of the ultrasonic energy from the signal may be reflected by the area of interest and the surrounding anatomy as ultrasound echoes. These ultrasound echoes may be received by the ultrasound transducer elements, as shown in more detail with reference to FIG. 4. The connector 224 may transfer the received echo signals to the PIM 150 and/or ultrasound processing system 160 where an ultrasound image based on the received echo signals is reconstructed and displayed on the monitor 170. In some embodiments, the ultrasound system 200 is used to generate two-dimensional and three-dimensional images. In some examples, the ultrasound system 200 may be used for generating X-plane images at two different viewing directions perpendicular to each other. In some embodiments, the PIM 150 may control the activation of the ultrasound transducer elements and the reception of the echo signals to generate various images from different viewpoints.

The tip member 202 may also be used for treating areas of interest within the anatomy of the patient. For example, the tip member 202 may be used to transmit ultrasound energy for treatment purposes, such as preparing areas of interest for the introduction of medication or for ultrasound cavitation. As discussed below, the ultrasound signals used for diagnostic purposes may be transmitted from a different section of the tip member 202 than the ultrasound signals used for therapeutic purposes.

In some embodiments, a button, toggle, or switch 211 is disposed on the handle 220 and may be used to toggle between a diagnostic functionality and a therapeutic functionality for the tip member 202. For example, an operator may activate the switch 211 to a "diagnostic mode" in which the tip member 202 transmits ultrasound signals and receives ultrasound echoes for diagnostic purposes. The operator may then activate the switch to a "therapeutic mode" in which the tip member 202 transmits ultrasound signals for therapeutic purposes, without receiving ultrasound echoes. In other embodiments, the tip member 202 may be used for diagnostic and therapeutic purposes simultaneously, such as transmitting ultrasound signals to treat an area of interest while simultaneously imaging the area of interest.

The ultrasound system 200 may be utilized in a variety of applications such as transseptal punctures, left atrial appendage closures, atrial fibrillation ablation, and valve repairs and can be used to image vessels and structures within a living body. Although the ultrasound system 200 is described in the context of intraluminal imaging procedures, the ultrasound system 200 may be suitable for use with any catheterization procedure, e.g., ICE. In addition, the tip member 202 may include any suitable physiological sensor or component for diagnostic, treatment, and/or therapy. For example, the tip member 202 may include imaging components, an ablation component, a cutting component, a morcellation component, a cavitation component, a pressure-sensing component, a flow-sensing component, a temperature-sensing component, and/or combinations thereof.

Figure 3:
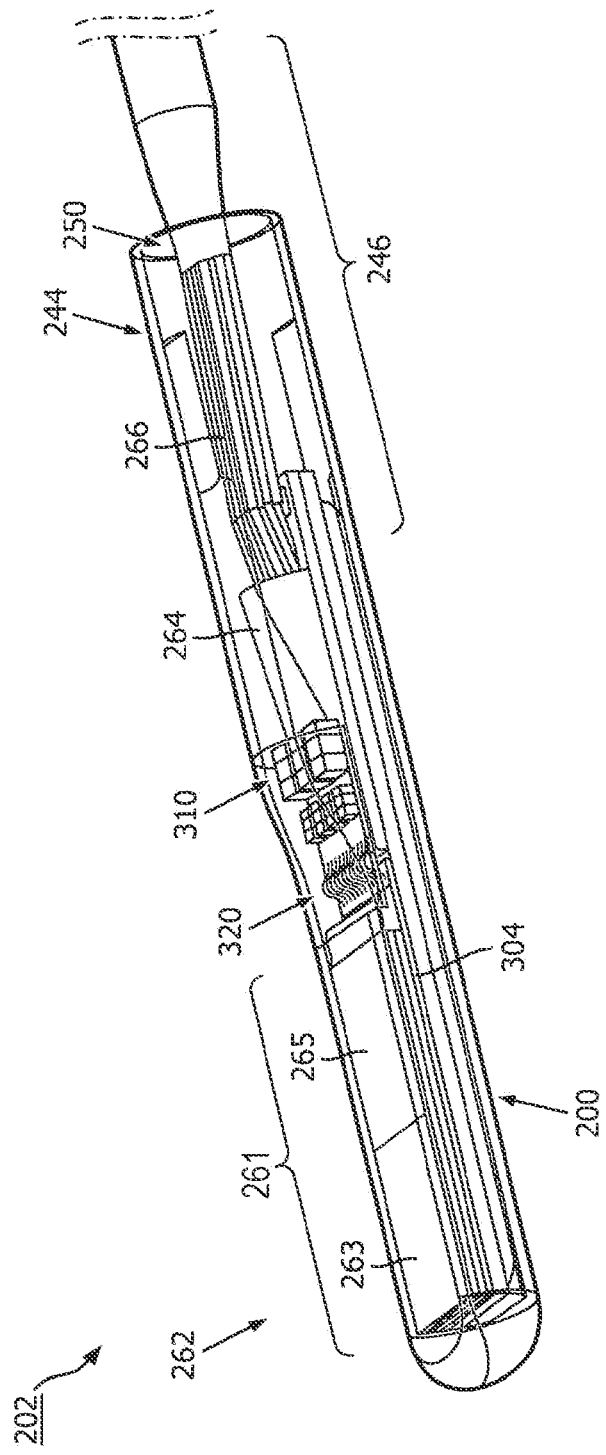
FIG. 3 is a top view of a tip member according to embodiments of the present disclosure.

FIG. 3 is a perspective view of the tip member 202 described above with respect to FIG. 2. The tip member 202 may include an imaging core 262 that is positioned at a distal portion of the tip member 202. The imaging core 262 may be coupled to an electrical cable 266 via an electrical interconnection 264. The electrical cable 266 may extend through the alignment portion 244 and the interface portion 246 of the inner cavity 250. The electrical cable 266 can further extend through the flexible elongate member 108 as shown in FIG. 1.

The configuration and structure of the tip member 202 may provide several benefits. The benefits include providing safe and easy delivery of the catheter, providing improved tensile strength for steering and navigation, providing consistent alignment, and providing improved image quality. For example, the outer geometry of the tip member 202 may be configured to provide smooth surfaces and smooth edges with small radii. The smooth edges reduce friction when the tip member 202 traverses a vessel during insertion. The smooth surfaces prevent tears and/or damages to tissue structures during the insertion. In addition, the smooth edges and smooth surfaces can facilitate crossing of a septum or other anatomical feature during a catheterization procedure. In some embodiments, the material type and the wall thickness of the tip member 202 are selected to minimize acoustic distortion, attenuation, and/or reflection. The internal geometry of the tip member 202 is configured to facilitate alignment during manufacturing. The tip member 202 can also include other features, for example, a guidewire lumen, one or more holes, or other geometry to accommodate additional devices or features such as pressure sensors, drug delivery mechanisms, and/or any suitable interventional features.

The imaging core 262 may include a transducer array 261 including one or more transducers as well as a controller 304 connected to the transducer array 261. The transducer array 261 may be configured to transmit ultrasound signals into the anatomy of the patient. In some embodiments, the transducer array 261 operates with intravascular ultrasound (IVUS) modality and is configured to provide data for IVUS images. In some embodiments, the transducer array 261 is configured to produce IVUS virtual histology (VH) images. Detecting and characterizing plaque using IVUS with VH are described in, for example, U.S. Pat. No. 6,200,268 entitled "VASCULAR PLAQUE CHARACTERIZATION" issued Mar. 13, 2001 with D. Geoffrey Vince, Barry D. Kuban and Anuja Nair as inventors, U.S. Pat. No. 6,381,350 entitled "INTRAVASCULAR ULTRASONIC ANALYSIS USING ACTIVE CONTOUR METHOD AND SYSTEM" issued Apr. 30, 2002 with Jon D. Klingensmith, D. Geoffrey Vince and Raj Shekhar as inventors, U.S. Pat. No. 7,074,188 entitled "SYSTEM AND METHOD OF CHARACTERIZING VASCULAR TISSUE" issued Jul. 11, 2006 with Anuja Nair, D. Geoffrey Vince, Jon D. Klingensmith and Barry D. Kuban as inventors, U.S. Pat. No. 7,175,597 entitled "NON-INVASIVE TISSUE CHARACTERIZATION SYSTEM AND METHOD" issued Feb. 13, 2007 with D. Geoffrey Vince, Anuja Nair and Jon D. Klingensmith as inventors, U.S. Pat. No. 7,215,802 entitled "SYSTEM AND METHOD FOR VASCULAR BORDER DETECTION" issued May 8, 2007 with Jon D. Klingensmith, Anuja Nair, Barry D. Kuban and D. Geoffrey Vince as inventors, U.S. Pat. No. 7,359,554 entitled "SYSTEM AND METHOD FOR IDENTIFYING A VASCULAR BORDER" issued Apr. 15, 2008 with Jon D. Klingensmith, D. Geoffrey Vince, Anuja Nair and Barry D. Kuban as inventors and U.S. Pat. No. 7,463,759 entitled "SYSTEM AND METHOD FOR VASCULAR BORDER DETECTION" issued Dec. 9, 2008 with Jon D. Klingensmith, Anuja Nair, Barry D. Kuban and D. Geoffrey Vince, as inventors, the teachings of which are hereby incorporated by reference herein in their entireties.

In some embodiments, the controller 304 is a micro-beam-forming integrated circuit (IC). The controller may directly control the transmission and reception of ultrasound signals by the transducer array, including switching between diagnostic and therapeutic modes. In some embodiments, the transducer array 261 is mounted directly on the controller 304 and is electrically connected to the transducer array 261. The controller 304 may be disposed on a core element with a round shape. In some embodiments, elements of the transducer array 261 may be attached to the controller 304 by flip-chip mounting or grown directly on top of the controller 304. In some embodiments, an electrical cable 266 may be terminated directly to the controller 304, or may be terminated to an interposer 310 of suitable material such as a rigid or flexible printed circuit assembly. The interposer 310 may then be connected to the controller 304 via any suitable means such as wire bondings 320.

In some embodiments, the transducer array 261 includes a two-dimensional, rectangular matrix array with a number of transducer elements. The transducer array 261 may also include one or more one-dimensional array components. The transducer array 261 may include materials such as PZT, PZT composites, CMUT, PMUT, single crystals, or any combination of these. The transducer elements of the transducer array 261 may be piezoelectric or micromachined ultrasonic transducer (MUT) elements. The transducer array 261 may include an active area in which signals are transmitted and received by transducer elements. The transducer array 261 may also include inactive areas such as the underside of the array or edges of the array where mounting device are disposed. In some embodiments, the transducer array 261 comprises 800 or more transducer elements. In other embodiments, the transducer array 261 may include between 32 and 1000 transducer elements. For example, the transducer array can include 32, 64, 128, 256, 512, 640, 768, or any other suitable number of transducer elements. For example, a one-dimensional array may have 32 transducer elements and a two-dimensional array may have 32, 64, or more transducer elements. In other embodiments, the transducer array 261 may have other shapes, such as square, elliptical, circular, or irregular shapes. The shape of the active area of the transducer array 261 may include multiple alternating columns and rows and/or concentric circles or other shapes.

In some embodiments, the tip member 202 may include a transducer array 261 connected to the PIM 150 with fewer than 30 wires that include signal lines, power lines, and control lines. In some embodiments, the 30 wires or less include 6-12 signal lines, preferably include 8 signal lines. In other embodiments, the number of signal lines is between 10 and 20, for example, 12 signal lines, 16 signal lines, or any other suitable number of signal lines.

In some examples, the transducer array 261 is configured for two-dimensional and three-dimensional imaging. For example, a one-dimensional portion of the transducer array 261 may be used to generate two-dimensional images while a two-dimensional portion of the transducer array 261 may be used to generate two- or three-dimensional images.

In some embodiments, the transducer array 261 may be similar to the ultrasound transducer array of structure 130 as shown in FIG. 1. In particular, the transducer array 261 may be configured to generate signals within a tunable range of 1 kHz and 70 MHz. In some embodiments, the first segment 263 of the transducer array 261 may be configured to provide signals for diagnostic procedures and the second segment 265 may be configured to provide signals for therapeutic procedures. For example, the first segment 263 may be configured to transmit ultrasound signals at an area of interest and receive reflected ultrasound echoes. The first segment 263 may be connected to processing systems (such as the ultrasound processing system 160 as shown in FIGS. 1 and 2) via the electrical cable 266 such that the reflected ultrasound echoes can be processed into one or more images of the area of interest. The second segment 265 may be configured to transmit ultrasound signals for therapeutic purposes and may not be configured to receive reflected ultrasound echoes.)

In some embodiments, the first segment 263 is populated with a high resonant frequency material and the second segment 265 is populated with a low resonant frequency material. In some embodiments, these materials include different compositions. In other embodiments, these materials include the same composition but the voltage applied to the first segment 263 is not the same as the voltage applied to the second segment 265.

Although in the example of FIG. 3 the transducer array 261 includes only a first segment 263 and a second segment 265, in other embodiments, more segments may be included. For example, the transducer array 261 may include 1, 3, 4, 5, 6 or other numbers of segments which may be used to transmit ultrasound signals with different ranges of frequencies.

Figure 4:
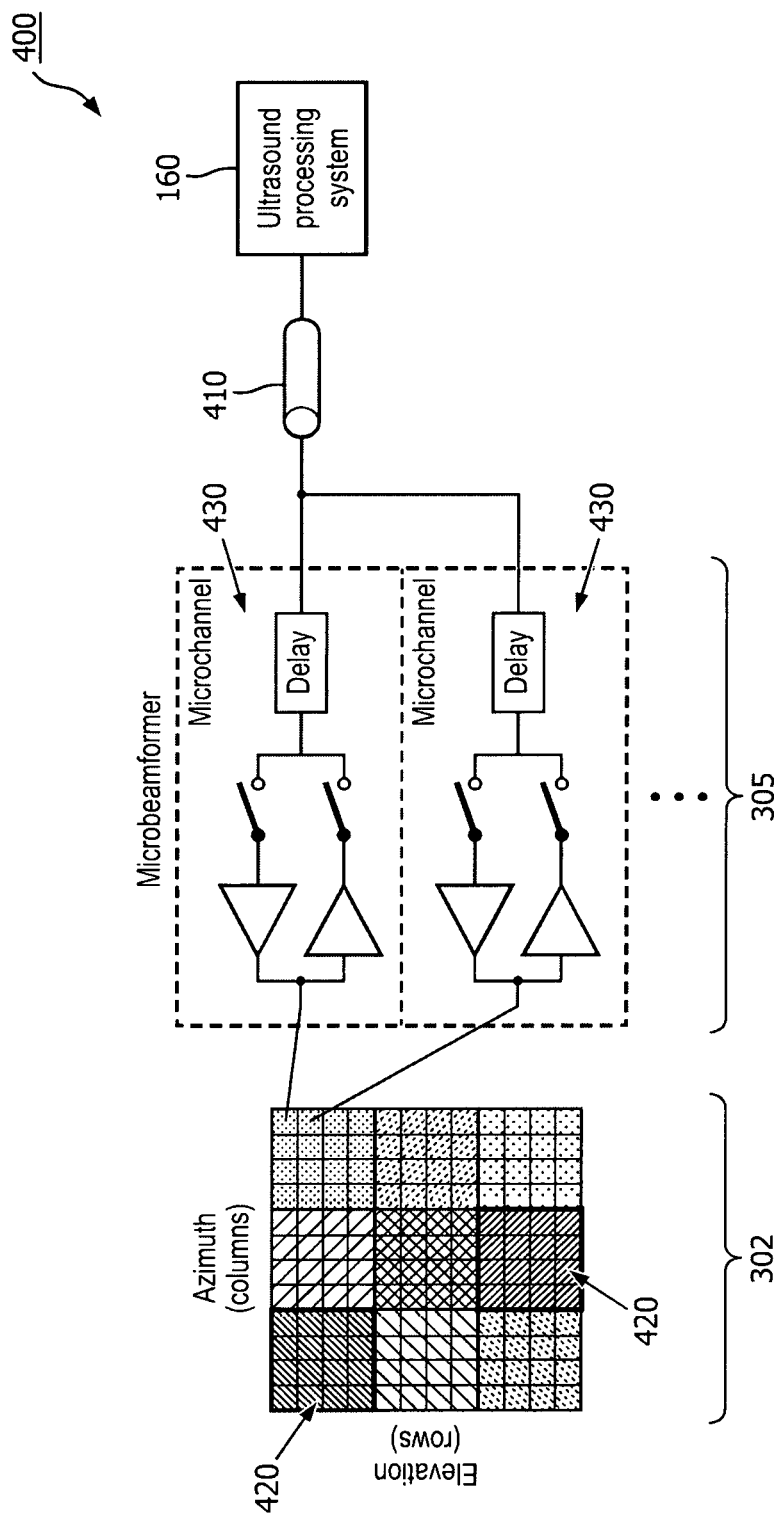
FIG. 4 is a schematic diagram illustrating the beamforming of an ultrasound device according to embodiments of the present disclosure.

FIG. 4 is a schematic diagram 400 illustrating the beam-forming of an ultrasound system according to embodiments of the present disclosure. Beam-forming of ultrasound signals can occur before ultrasound signals are transmitted by the transducer array 261 or after the ultrasound echoes are received by the transducer array 261. Embodiments of the present disclosure, such as the beam-forming applications of the present disclosure, may include features similar to those described in U.S. Provisional App. No. 62/403,479 filed Oct. 3, 2016 and U.S. Provisional App. No. 62/434,517 filed Dec. 15, 2016, U.S. Provisional App. No. 62/403,311 filed Oct. 3, 2016 and U.S. Provisional App. No. 62/437,778 filed Dec. 22, 2016, U.S. Provisional App. No. 62/401,464, filed Oct. 29, 2016, U.S. Provisional App. No. 62/401,686, filed Oct. 29, 2016, and/or U.S. Provisional App. No. 62/401,525, filed Oct. 29, 2017, the entireties of which are hereby incorporated by reference herein.

The diagram 400 includes the tip member 202 including an array of transducer elements 302 and a micro-beamformer IC 305. In some embodiments, the array of transducer elements 302 forms a portion of the transducer array 261. The micro-beam-former IC 305 may be part of the controller 304, or alternatively, a separate component that this connected to the transducer array 261. The micro-beam-former IC 305 may be coupled to the array of transducer elements 302 at the distal portion of the ultrasound device 210. As shown, the array of transducer elements 302 is divided into one or more subarrays of transducer elements 420. For example, the array of transducer elements 302 may be divided into nine subarrays of transducer elements 420 that each has 16 transducer elements arranged as 4 by 4. In some embodiments, the first segment 263 and second segment 265 may include one or more subarrays of transducer elements 420.

The micro-beam-former IC 305 may include a plurality of microchannels 430 that may each separately beam-form the signals received from transducer elements of a corresponding subarray of transducer elements 420. As shown in FIG. 4, for example, the microchannels 430 each comprise a delay for alignment of the signals received from the transducer elements of a subarray of transducer elements 420. As shown, the microchannels delay lines 430 of each subarray of transducer elements 420 may be separately coupled to one coaxial cable 410 such that the received signals of each subarray of transducer elements 420 are transferred through a separate channel, e.g., coaxial cable 410, to the ultrasound processing system 160.

In some embodiments, the micro-beam-former IC 305 is configured to control the array of transducer elements 302. For example, the micro-beam-former IC 305 may control the activation of particular transducer elements of the array of transducer elements 302 as well as controlling the angle at which ultrasound signals are transmitted by the transducer elements. The micro-beam-former IC 305 may also control the frequency of transmitted ultrasound signals. Furthermore, the micro-beam-former IC 305 may perform beam forming for a plurality of transducer elements of each of the subarrays of transducer elements 420 of the array of transducer elements 302.

In some embodiments, the tip member 202 includes an electrical cable 266 that includes two or more signal lines that are coupled to the micro-beam-former IC 305. Each of signal lines is associated with one of the subarrays of transducer elements 420 of the array of transducer elements 302 to transfer beam formed imaging signals of the associated subarray. For example, each signal line corresponds to a particular subarray of transducer elements 420 and is configured to receive the beam-formed signals specific to the corresponding subarray.

In some embodiments, the electrical cable 266 further includes one or more power lines for feeding power to the micro-beam-former IC 305 and one or more control lines for communicating control signals to the micro-beam-former IC 305.

In some embodiments, the micro-beam-former IC 305 includes multiple microchannel delay lines 430. The microchannel delay lines 430 are used to perform the beam forming for the plurality of transducer elements of each of the two or more subarrays of transducer elements 420. In some examples, the multiple microchannel delay lines 430 include at least one of a charge coupled device, an analog random access memory, or a tapped analog delay line. In some examples, the first beam-formed signals and the second beam-formed signals are transmitted via a connection cable to the ultrasound processing system 160 of FIGS. 1 and 2.

Figure 5:
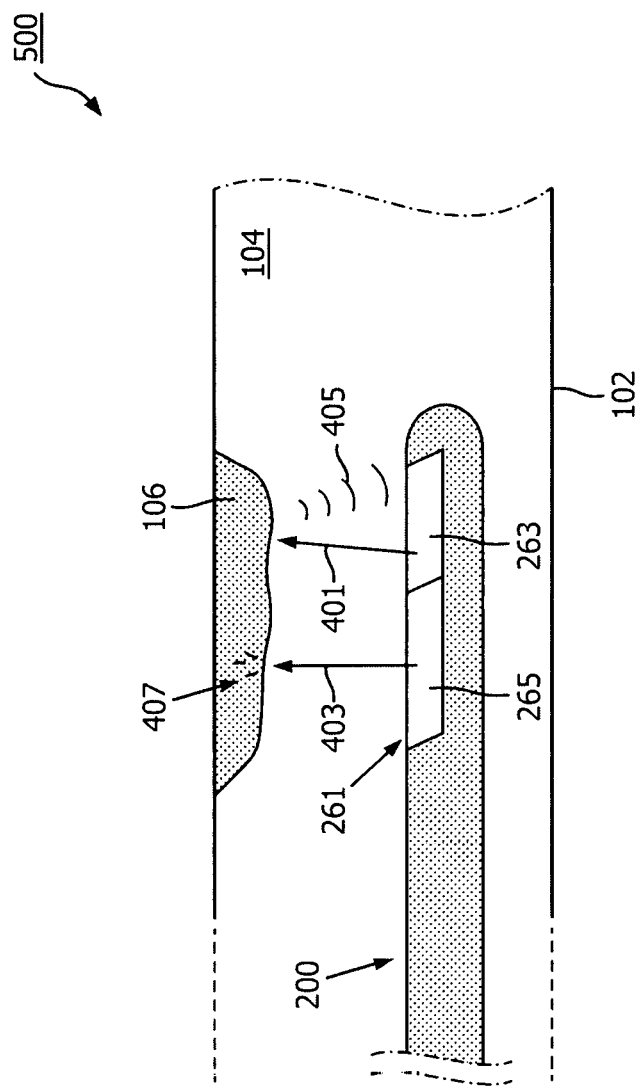
FIG. 5 is a schematic diagram illustrating aspects of an ultrasound device according to embodiments of the present disclosure.

FIG. 5 is a diagrammatic schematic view 500 of a tip member 202 of an ultrasound system 200 within the anatomy 102 of a patient. As discussed above, the tip member 202 may include a transducer array 261 including a first segment 263 and a second segment 265. In some embodiments, the first segment 263 of the imaging core 262 is configured to transmit signals 401 into the anatomy 102 for diagnostic purposes. These signals may reflect off various formations in the anatomy and ultrasound echoes 405 may be produced. The first segment 263 may also be configured to receive the ultrasound echoes 405 associated with the signals 401. These ultrasound echoes may be transmitted to processing systems (such as the ultrasound processing system 160 as shown in FIGS. 1 and 2) to produce images of the anatomy 102.

The second segment 265 may be configured to transmit signals 403 for therapeutic procedures. For example, the signals 403 may be transmitted to treat a portion of the anatomy 102, such as an occlusion 106 with a vessel 104 as shown in FIG. 4. The signals 403 may create micro fractures 407 in the occlusion 106, which may aid in treating the occlusion 106. The signals 401, 403 may be transmitted from different angles without moving the tip member 202. In some embodiments, the micro fractures 407 may weaken or soften the occlusion 106 which may be entirely removed in another procedure.

Figure 6:
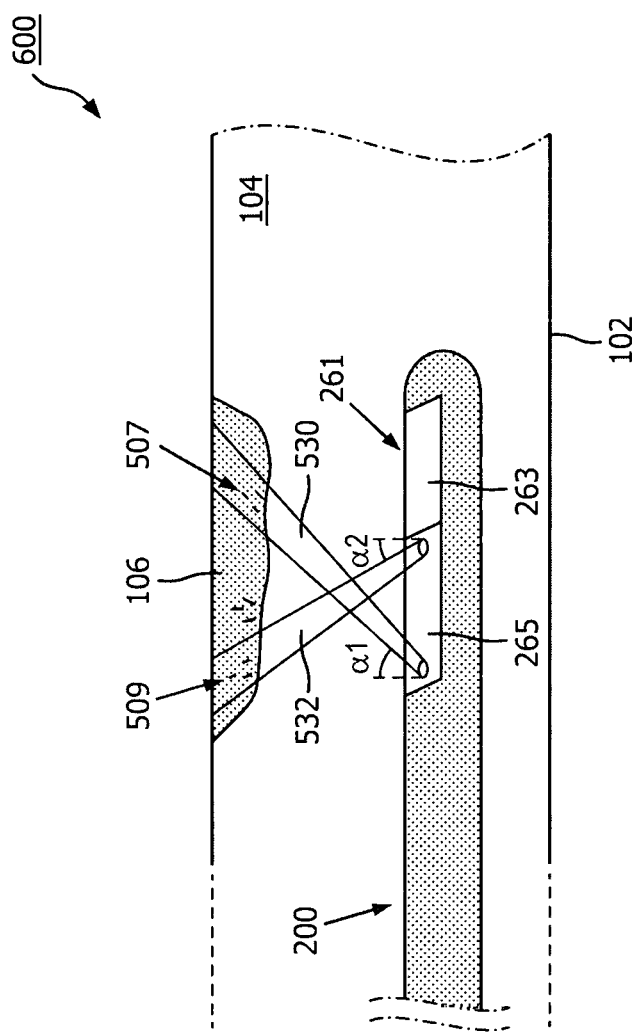
FIG. 6 is another schematic diagram illustrating aspects of an ultrasound device according to embodiments of the present disclosure.

FIG. 6 is another diagrammatic schematic view 600 of a tip member 202 within the anatomy 102 of a patient. The transducer array 261 on the tip member 202 may be configured to transmit ultrasound signals from different areas of the transducer array 261. Furthermore, the transducer array 261 may be configured to allow control over various parameters of the pulses, such as frequency, pulse amplitude, pulse length, signal pattern, and transmission angle. These parameters may be controlled by an automated process or a user controlled process. This may allow the transducer array 261 to image and provide optimized treatment to various portions of the anatomy without moving the tip member.

In some embodiments, the first segment 263 and the second segment 265 of the transducer array 261 may be configured for transmitting ultrasound signals at different angles. In the example of FIG. 6, ultrasound signals 530 are transmitted with an angle $\alpha 1$. The ultrasound signals are directed at a first area of interest. Ultrasound signals 532 may be transmitted with angle $\alpha 2$ and may be directed at a second area of interest. Angle $\alpha 2$ may be different than $\alpha 1$ and ultrasound signals 532 may be transmitted from a different location on the transducer array 261 than ultrasound signals 530. In some embodiments, the ultrasound signals 530, 532 may be used for cavitation and may create micro fractures 507, 509 in the anatomy. Since the ultrasound signals 530, 532 are transmitted at different angles, the micro fractures 507, 509 may have different orientations. This may allow an operator make various angular ultrasound cuts into areas of interest (such as calcification or plaque) without moving the tip member 202. The transducer array 261 may also provide frequency and power optimization to control the depth of cuts which may allow for precise cavitation procedures. Ultrasound signals may be transmitted with varying amplitudes, widths, and shapes by varying the ultrasound transducer elements used to transmit the ultrasound signals. For example, a controller may be used to activate a large number of transducer elements in a circular pattern which may result in the transmission of a large cylindrical or conical signal pattern. Alternatively, the controller may be used to activate a small number of ultrasound elements in a rectangular pattern which may result in the transmission of a small, rectangular or pyramidal signal pattern. The strength and frequency of ultrasound signals in these patterns may also be varied.

Figure 7:
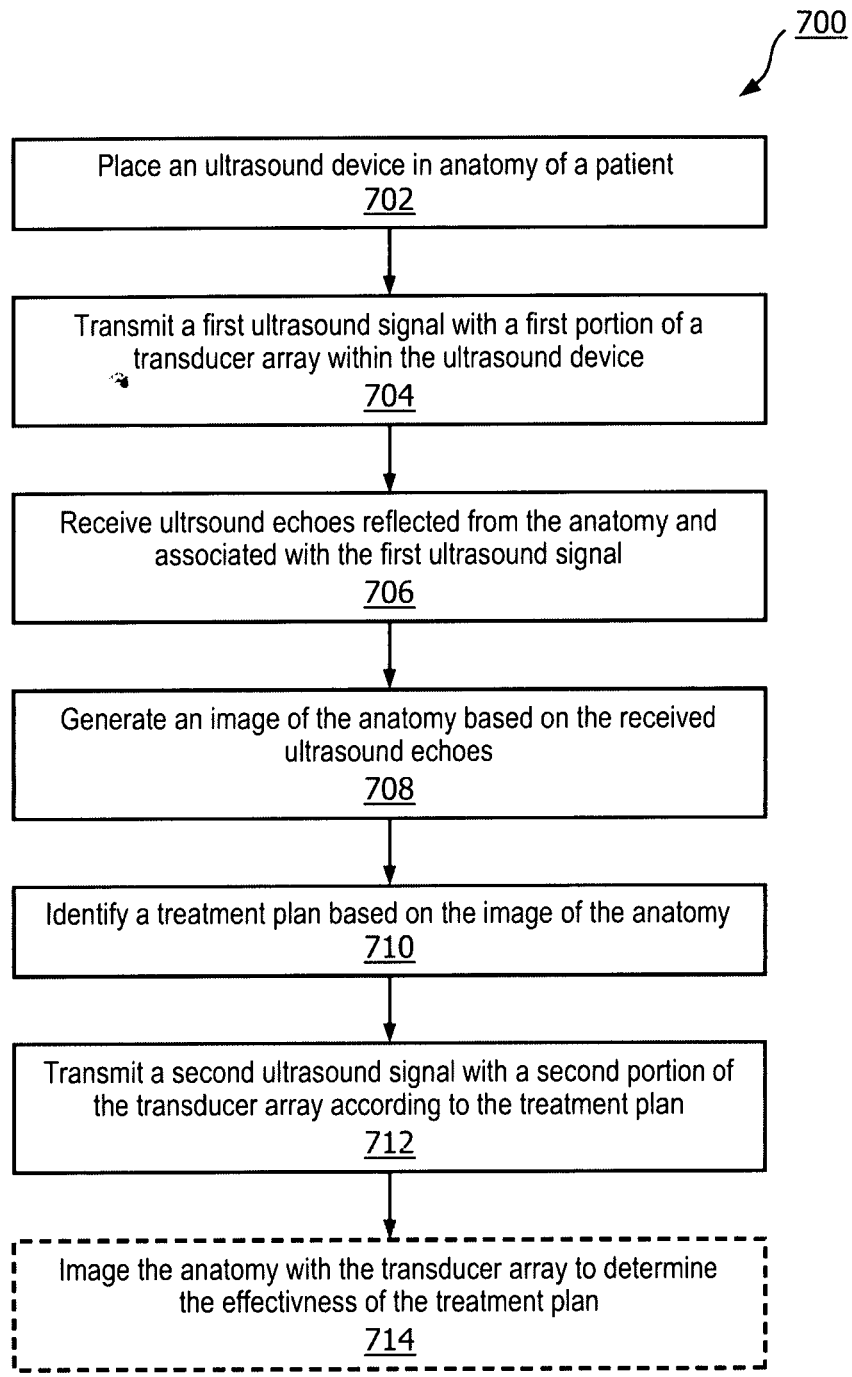
FIG. 7 is a flowchart illustrating a method of transmitting ultrasound signals according to embodiments of the present disclosure.

FIG. 7 provides a flow diagram illustrating a method 700 of transmitting ultrasound signals. As illustrated, the method 700 includes a number of enumerated steps, but embodiments of the method 700 may include additional steps before, after, and in between the enumerated steps. In some embodiments, one or more of the enumerated steps may be omitted, performed in a different order, or performed concurrently. The method 700 may be performed using any of the systems and devices referred to in FIGS. 1-6.

At step 702, the method 700 may include placing an ultrasound device in anatomy of a patient. The ultrasound device may be the ultrasound device 210 including the tip member 202 as shown in FIG. 2. In other embodiments, the ultrasound device may be a rotational, flat phased array, or circumferential phased array device. In some embodiments, an operator may use a handle such as handle 220 as shown in FIG. 2 to manipulate an elongate flexible member of the ultrasound device 210 to an area of interest in the anatomy, such as a vessel or chamber of the heart. The ultrasound device may be used to image the anatomy of the patient during the manipulation of the ultrasound device, such as to aid the operator in maneuvering through the vasculature of the patient.

At step 704, the method 700 may include transmitting a first ultrasound signal with a first portion of a transducer array within the ultrasound device. The first ultrasound signal may be transmitted while the ultrasound device is in a diagnostic mode. In some embodiments, the transducer array is disposed on a tip member on a distal portion of the ultrasound device. In some embodiments, the first portion of the transducer array includes a number of transducer elements which may be controlled independently. The first ultrasound signal may be directed at various angles to a portion of the anatomy without physically moving the tip member. The first ultrasound signal (and subsequent signals) may be sent with a tunable wave range to optimize visualization of the anatomy. For example, an operator may be able to change the frequency of each signal based on the measured anatomy and the desired imaging or therapeutic effects of the signal. The first ultrasound signal may be reflected off the anatomy in the form of ultrasound echoes, some of which may travel back toward the transducer array.

At step 706, the method 700 may include receiving ultrasound echoes reflected from the anatomy and associated with the first ultrasound signal. The ultrasound echoes may be received by the same portion of the transducer array that transmitted the first ultrasound signal. In some embodiments, the data from the ultrasound echoes may be analyzed by a controller within the ultrasound device (such as adjacent to the transducer array) or communicated by a cable or other means to a processing device outside the patient. In some embodiments, the transducer array may be an intravascular ultrasound (IVUS) array that is configured to transmit and receive IVUS signals.

At step 708, the method 700 may include generating an image of the anatomy based the received ultrasound echoes. The image of the anatomy may be a two- or three-dimensional image of the anatomy. In some embodiments, the image is an IVUS VH image. The image of the anatomy may be displayed on a display device such as a computer monitor. The image may be accompanied by measured data, such as data on the diameter, calcification, and density of vessels and other anatomical structures. In some embodiments, the age and hardness of calcium may be measured by the system through analysis of the images of the anatomy.

At step 710, the method 700 may include identifying a treatment plan based on image of the anatomy. In some embodiments, the image of the anatomy may be analyzed by the system automatically to detect problems (i.e., calcification, occlusions, plaques, abnormalities in the anatomy, etc.). The system may be used to identify a treatment plan based on problems in the image. In some embodiments, the treatment plan may include a therapeutic procedure to be performed by the ultrasound device.

At step 712, the method 700 may include transmitting a second ultrasound signal with a second portion of the transducer array according to the treatment plan. The second ultrasound signal may be transmitted while the ultrasound device is in a cavitation or therapeutic mode. The mode of the ultrasound device may be switched by an operator, such as by using the switch 211 as shown in FIG. 2. The second portion of the transducer array may be adjacent to the first portion and may include a number of transducer elements. In some embodiments, the second portion is configured to transmit ultrasound signals but not receive ultrasound signals. In some embodiments, an optical frequency, pulse amplitude, and pulse length of the second ultrasound signal may be determined by a controller based on the treatment plan identified in step 710. The second ultrasound signal may have a frequency lower than that of the first ultrasound signal. In some embodiments, the second ultrasound signal is transmitted to perform a therapeutic procedure such as creating micro fractures in the anatomy and/or treating the anatomy in preparation for delivery of a drug. The second signal may be transmitted at varying angles or frequencies. The second portion of the transducer array may be used to transmit other ultrasound signals, such that a pattern of fractures with different angles may be produced in a portion of the anatomy without moving the transducer array. In some embodiments, step 712 may be repeated to carry out one or more therapeutic procedures. In particular, the ultrasound device may be switched to different modes and transmit different ultrasound signals. For example, a second ultrasound signal may be transmitted to prepare a vessel for a treatment. A third ultrasound signal (or a further series of ultrasound signals) may then be transmitted to perform the treatment, such as creating micro fractures within an occlusion.

At step 714, the method 700 may optionally include imaging the anatomy with the transducer array to determine the effectiveness of the treatment plan. In some embodiments, the mode of the ultrasound device may be switched from therapeutic mode to diagnostic mode for this step. In some embodiments, the first portion may be used to transmit another ultrasound signal and receive the reflected ultrasound echoes to determine if the desired effect has been achieved. In some embodiments, the ultrasound device may be used to image anatomy after treatment to identify further problem areas or conditions (such as identifying emboli in the anatomy after a procedure). The steps of method 700 may be repeated to identify treatment plans, carry out the treatment plans, and determine the effectiveness of treatment. In some embodiments, the ultrasound device may be changed from diagnostic to therapeutic modes throughout the procedures. Other therapeutic procedures may also be used to treat the patient during and after these steps, such as dilating diseased areas using a balloon catheter, placing correctly sized stents, and delivering drugs.

The systems, devices, and methods of the present disclosure can include features described in U.S. Provisional App.

No. 62/545,944 filed Aug. 15, 2017, U.S. Provisional App. No. 62/545,951 filed Aug. 15, 2017, filed on an even date herewith, U.S. Provisional App. No. 62/545,954 filed Aug. 15, 2017, filed on an even date herewith, and/or U.S. Provisional App. No. 62/545,888 filed Aug. 15, 2017, filed on an even date herewith, the entireties of which are hereby incorporated by reference herein.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound system, comprising:
a flexible elongate member configured to be positioned within vasculature of a patient adjacent to an occlusion, the flexible elongate member comprising a proximal portion and a distal portion;
an ultrasound transducer array positioned at the distal portion of the flexible elongate member, wherein the ultrasound transducer array includes a plurality of independently-controlled transducer elements arranged in a first segment and a second segment, wherein the first segment is configured to emit a first ultrasound signal within a first frequency range between 10 MHz and 70 MHz and to receive ultrasound echoes reflected from the vasculature and associated with the first ultrasound signal within the first frequency range for diagnostic use, imaging of at least the occlusion, wherein the second segment is configured to emit a second ultrasound signal within a second frequency range between 20 kHz and 3 MHz for therapeutic use, including damaging a structure of the occlusion shown in the imaging;
a beamforming controller at the distal portion of the flexible elongate member, wherein the beamforming controller is configured to independently drive each of the plurality of independently-controlled transducer elements, the beamforming controller comprising an integrated circuit (IC) configured to control an angle of transmission of at least the second ultrasound signal by the second segment for producing a pattern of fractures in the occlusion with different angles, without moving the ultrasound transducer array, for damaging the structure of the occlusion, wherein the IC includes a plurality of microchannels each configured to separately beam form signals received from the independently-controlled transducer elements in the first segment, each microchannel including a delay configured to align the signals received from the independently-controlled transducer elements, the delay comprises at least one of a charge coupled device, an analog random access memory, or a tapped analog delay line; and
a plurality of signal lines coupling each of the independently-controlled transducer elements in the ultrasound transducer array to the beamforming controller.

2. The ultrasound system of claim 1, wherein the ultrasound transducer array is a two-dimensional array of the independently controlled transducer elements, wherein the first segment comprises a first plurality of the independently controlled transducer elements disposed on a first portion of the two-dimensional array and in communication with the beamforming controller via a first one of the signal lines, and wherein the second segment comprises a second plurality of the independently controlled transducer elements disposed on a second portion of the two-dimensional array adjacent the first portion and in communication with the beamforming controller via a second one of the signal lines.

3. The ultrasound system of claim 1, wherein the ultrasound transducer array comprises at least one of a lead zirconate titanate (PZT) transducer, a capacitive micromachined ultrasound transducer (CMUT), and a piezoelectric micromachined ultrasonic transducer (PMUT).

4. The ultrasound system of claim 1, wherein the ultrasound transducer array is configured to direct the second ultrasound signal to a first portion of occlusion and a second portion of occlusion different from the first portion of anatomy without moving the ultrasound transducer array.

5. The ultrasound system of claim 1, further comprising a switch to selectively switch between transmitting the first ultrasound signals with the first segment and transmitting the second ultrasound signals with the second segment.

6. The ultrasound system of claim 1, further comprising a substrate including electrical conductors connected to the ultrasound transducer array, the electrical conductors configured to selectively switch between transmitting signals with the first segment and the second segment.

7. The ultrasound system of claim 1, wherein the flexible elongate member comprises a first cable configured to control transmission of the first ultrasound signals of the first segment and a second cable configured to control transmission of the second ultrasound signals of the second segment.

8. The ultrasound system of claim 7, wherein the flexible elongate member comprises a third cable configured to control transmission of both the first and second ultrasound signals of the first segment and the second segment.

9. The ultrasound system of claim 1, further comprising:
a treatment component positioned at the distal portion of the flexible elongate member adjacent to the ultrasound transducer array, wherein the treatment component is configured to apply a treatment to the occlusion following the producing of the pattern of fractures in the occlusion by the second ultrasound signal.

10. The ultrasound system of claim 9, wherein the treatment component comprises a targeted drug delivery device, a drug coated balloon or a drug coated stent configured to deliver a pharmacological agent to the occlusion.

11. The ultrasound system of claim 9, wherein the treatment component comprises a balloon, a stent, a needle, an ablation electrode, a mechanical cutting component, a rotational cutting device, or an aspiration device.

* * * * *